(12) United States Patent
Kohda et al.

(10) Patent No.: US 7,924,400 B2
(45) Date of Patent: Apr. 12, 2011

(54) METHOD FOR MEASURING LIQUID IMMERSION LITHOGRAPHY SOLUBLE FRACTION IN ORGANIC FILM

(75) Inventors: Nobuyuki Kohda, Kawasaki (JP); Masaaki Yoshida, Kawasaki (JP); Takayuki Yajima, Kawasaki (JP); Hiromitsu Tsuji, Kawasaki (JP)

(73) Assignee: Tokyo Ohka Kogyo Co., Ltd., Kanagawa (JP)

( * ) Notice: Subject to any disclaimer, the term of this patent is extended or adjusted under 35 U.S.C. 154(b) by 479 days.

(21) Appl. No.: 12/067,925

(22) PCT Filed: Sep. 25, 2006

(86) PCT No.: PCT/JP2006/318994
§ 371 (c)(1),
(2), (4) Date: Mar. 24, 2008

(87) PCT Pub. No.: WO2007/034949
PCT Pub. Date: Mar. 29, 2007

(65) Prior Publication Data
US 2009/0268173 A1    Oct. 29, 2009

(30) Foreign Application Priority Data

Sep. 26, 2005  (JP) ................................. 2005-277116
Feb. 15, 2006  (JP) ................................. 2006-038280

(51) Int. Cl.
*G03B 27/52*    (2006.01)
*G03B 27/42*    (2006.01)

(52) U.S. Cl. .......................................... 355/30; 355/53
(58) Field of Classification Search .................. 355/30, 355/52, 53, 77; 436/146, 177–178
See application file for complete search history.

(56) References Cited

U.S. PATENT DOCUMENTS

| | | | | |
|---|---|---|---|---|
| 4,990,459 A * | 2/1991 | Maeda et al. | ................. | 436/178 |
| 5,055,413 A * | 10/1991 | Kageyama et al. | ........... | 436/178 |
| 5,426,057 A * | 6/1995 | Tamaoki | ........................ | 436/146 |
| 5,610,683 A * | 3/1997 | Takahashi | ........................ | 355/53 |
| 7,317,507 B2 * | 1/2008 | Straaijer | ........................ | 355/53 |
| 7,399,635 B2 * | 7/2008 | Hellin et al. | ........................ | 436/5 |

FOREIGN PATENT DOCUMENTS

| | | |
|---|---|---|
| JP | H02-028533 A | 1/1990 |
| JP | H10-303114 A | 11/1998 |
| JP | 2944099 B | 8/1999 |

(Continued)

OTHER PUBLICATIONS

Omori, Katsumi et al., "New Cover Material Development Status for Immersion Lithography", Oct. 28, 2004, Anti-Reflective Coatings Symposium 2004. Taiwan Patent Application No. 095135286, Office Action, mailed Feb. 17, 2009.

*Primary Examiner* — Hung Henry Nguyen
(74) *Attorney, Agent, or Firm* — Stephen C. Beuerle; Procopio Cory Hargreaves & Savitch LLP

(57) ABSTRACT

A method for measuring a liquid immersion lithography soluble fraction in an organic film including a mounting step of mounting a droplet of a liquid immersion medium for liquid immersion lithography on a surface of an organic film formed on a substrate; and a transfer step of transferring a component in the organic film into the droplet.

10 Claims, 4 Drawing Sheets

FOREIGN PATENT DOCUMENTS

| | | |
|---|---|---|
| JP | H11-218474 A | 8/1999 |
| JP | 2005-079238 A | 3/2005 |
| JP | 2005-101498 A | 4/2005 |
| JP | 2005-135949 A | 5/2005 |
| JP | 2005-157259 A | 6/2005 |
| WO | WO-2004/074937 A1 | 9/2004 |

* cited by examiner

METHOD FOR MEASURING LIQUID IMMERSION LITHOGRAPHY SOLUBLE FRACTION IN ORGANIC FILM

CROSS REFERENCE TO RELATED APPLICATION

This application claims priority to and the benefit of PCT Patent Application No. PCT/JP2006/318994, filed Sep. 25, 2006, which claims priority to Japanese Patent Application number 2005-277116, filed Sep. 26, 2005 and Japanese Patent Application number 2006-038280, filed Feb. 15, 2006. All of these applications/patent(s) are incorporated by reference as though set forth in full.

TECHNICAL FIELD

The present invention relates to a method for measuring a liquid immersion lithography soluble fraction in a photoresist composition, or an organic film provided on a top layer thereof such as a protective film when a liquid immersion lithography process is employed in a photolithography step for producing semiconductor elements and the like, particularly relates to a method for measuring a liquid immersion lithography soluble fraction for the purpose of measuring and evaluating with high accuracy an exuded component yielded by exudation from a photoresist film or a protective film into the liquid immersion medium in a liquid immersion exposure process in which the photoresist film, or the photoresist film provided with the protective film is exposed in such a state that a liquid (liquid immersion medium) having a predetermined thickness of which the refractive index is larger than air is interposed on the surface of the photoresist film or the protective film.

Furthermore, the present invention relates to a method for producing a material for forming an organic film which includes the measuring method described above as a quality control step in the production process, and also relates to a material for forming an organic film obtained by this method for production.

BACKGROUND OF THE INVENTION

Lithography methods have been frequently used for the production of fine features in various kinds of electronic devices such as semiconductor devices and liquid crystal devices. At present, the photolithography method allows the formation of a fine resist pattern having a line width of about 90 nm. However, finer resist pattern formation will be required in future with miniaturization of device structures. Therefore, development of a photoresist composition that meets such needs as formation of a fine pattern has been an urgent task.

As the electronic device structure is miniaturized, further enhancement of resolution of projection optics has been also demanded. The resolution of projection optics is enhanced as the shorter exposure wavelength is employed, or as the numerical aperture of the projection optics is increased. Thus, the wavelength of light used in an exposure device has been lowered year by year, and with this lowering, numerical aperture of the projection optics has been increasing. Meanwhile, currently dominant exposure wavelengths involve 248 nm for KrF excimer laser, and further short wavelength of 193 nm for ArF excimer laser. When the exposure is carried out, focal depth is also important similarly to the resolution. The resolution R and the focal depth δ are represented by the following formulae, respectively.

$$R = k_1 \cdot \lambda / NA \quad (1)$$

$$\delta = \pm k_2 \cdot n\lambda / (NA)^2 \quad (2)$$

$$NA = n \times \sin\theta \quad (3)$$

Wherein, $\lambda$ represents an exposure wavelength; NA represents a numerical aperture of the projection optics; $k_1$ and $k_2$ represent a process coefficient; n represents a refractive index of a medium through which the exposure light passes; and $\theta$ represents an angle formed by the exposure light. When the medium through which the exposure light passes is air, n is 1. NA is theoretically up to less than 1, and is actually at most about 0.9 ($\theta=65°$). From the above formula (1) and formula (2), it is proven that although the exposure wavelength $\lambda$ may be shortened and the numerical aperture NA may be increased for enhancing the resolution R, decrease in the focal depth $\delta$ is accompanied thereby.

When the focal depth is excessively decreased, the area which can be focused on the substrate surface with respect to the imaging plane of the projection optics becomes narrow, whereby the area in which a favorable resist pattern can be provided also becomes narrow. As a result, production of electronic devices could be difficult. Thus, as a method to shorten the exposure wavelength, and to increase the focal depth, liquid immersion process was proposed (for example, see Patent Documents 1 and 2). This liquid immersion process not only enhances the resolution but increases the focal depth to about n (n: refractive index of a liquid being usually about 1.2 to 1.6) times by filling in between the bottom face of the projection optics and the substrate surface with a liquid such as water or an organic solvent to utilize the alteration of the wavelength of the exposure light in the liquid to 1/n as compared with that into the air.

Outline of one example of the exposure device for the liquid immersion process is explained with reference to FIG. 6. FIG. 6 shows a schematic construction of the exposure device for the liquid immersion process. Exposure device 20 for this liquid immersion process includes mask stage 22 for supporting mask 21, substrate stage 24 for supporting substrate 23, illumination optics 25 for illuminating the mask 21 with an exposure light, projection optics 26 for projection exposure of a pattern image of the mask 21 illuminated by the exposure light to substrate 23 supported by the substrate stage 24, and control apparatus 27 for controlling the entire operation of the exposure device 20.

The mask stage 22 executes positioning of the mask 21 supported on the mask stage 22 via mask stage driving apparatus 28 that is controlled by the control apparatus 27, while the substrate stage 24 executes positioning of the substrate 23 supported on the substrate stage 24 via substrate stage driving apparatus 29 controlled by the control apparatus 27. Although not shown in the figure, organic films such as a photoresist film and a protective film as in the present invention are mounted on the substrate 23.

With respect to the light source for exposure used in the illumination optics 25, for example, lines in ultraviolet region emitted from a mercury lamp (g-ray, h-ray, i-ray), KrF excimer laser beams (wavelength 248 nm), ArF excimer laser beams (wavelength 193 nm), $F_2$ laser beams (wavelength 157 nm) and the like may be used. Of these, preferable light source provides ArF excimer laser beams. Reduced projection of the light passed through the mask 21 is conducted via the projection optics 26 to an exposure region on the substrate 23 at a predetermined projection magnification, whereby the exposure is performed.

In addition, the exposure device 20 for the liquid immersion process has liquid supply section 31 for supplying liquid immersion medium 30 on the substrate 23, and liquid recovery section 32 for recovery of the liquid immersion medium 30 on the substrate 23. This liquid immersion medium 30 is acceptable as long as it has a refractive index larger than the refractive index of air. The liquid supply section 31 and the liquid recovery section 32 are both controlled by the control apparatus 27, whereby the amount of liquid supply and the amount of liquid recovery on the substrate 23 per unit time are controlled.

In such exposure device 20 for the liquid immersion process, when, for example, pure water is used as the liquid immersion medium, the numerical aperture NA or the focal depth δ can be increased 1.44 times since pure water has a refractive index of 1.44 (in case of the light source providing ArF excimer laser (wavelength: 193 nm)). Therefore, when the liquid immersion process is adopted employing conventional projection optics, breakthrough of a barrier of a line width of 65 nm referred to as a limit in use of the ArF excimer laser is enabled without using $F_2$ laser beams (wavelength: 157 nm), and it is said that microfabrication to the line width of 45 nm can be theoretically achieved.

BRIEF SUMMARY OF THE INVENTION

Problems to be Solved by the Invention

However, pure water or other liquid is used as the liquid immersion medium in the exposure device for the liquid immersion process as described above, and the organic film such as the photoresist film or the protective film provided on the top layer thereof (see, Patent Document 6 and Nonpatent Document 1) is brought into direct contact with the liquid immersion medium in the exposure, whereby the organic film is invaded by the liquid immersion medium. Adverse affects on the liquid immersion medium from the organic film, and adverse affects on the organic film from the liquid immersion medium due to this invasion are responsible for exudation of the component constituting the organic film, from the organic film into the liquid immersion medium. Specifically, dissolution of the constituent component in the organic film into the liquid immersion medium leads to: alteration of the refractive index of the liquid immersion medium; dirty lens of the exposure device; and deterioration of the functions and the like inherent to the organic film resulting from exudation of the constituent component in the organic film into the liquid immersion medium. These affects may deteriorate size controllability of the resist pattern. Therefore, it is necessary that the exudation of the component from the organic film into the liquid immersion medium be strictly controlled.

Also, the inventors of the present application have developed, as a conventional method for analyzing the extent of exudation of the component from the organic film into the liquid immersion medium, a method which includes: mounting a liquid immersion medium on an organic film on a substrate to the extent that whole area of the organic film is covered (about 30 ml); allowing them to be in contact through elapse of a predetermined time (several minutes); thereafter collecting and concentrating the liquid immersion medium that contains the exuded component; and then employing a method for measuring the concentration of the exuded component using a mass spectrometer as a detector, whereby the degree of exudation of a variety of organic films is investigated/analyzed.

However, detection sensitivity to meet requirements in mass production of electronic devices has not been attained yet according to the conventional analysis methods, and thus more highly sensitive analysis procedure has been demanded.

Furthermore, in order to suppress exudation of the component from the photoresist film into the liquid immersion medium, to provide a protective film on the resist film was proposed (see, Patent Document 6 and Nonpatent Document 1). With respect to the protective film, it is certainly considerably more effective in suppressing the exudation from the photoresist film as compared with the case without providing the same.

However, the protective film is similarly unsatisfactory in terms of the detection sensitivity according to the conventional analysis method described above. Additionally, it is somewhat possible that its component or a degradation product, or a component of the photoresist film corresponding to the bottom layer or a degradation product thereof may be dissolved into the liquid immersion medium through the protective film. Therefore, similarly to the photoresist film, it is necessary to strictly control exudation of the component into the liquid immersion medium. Accordingly, more highly sensitive analysis procedure has been also demanded in connection with the protective film.

The present invention was made in view of the foregoing problems, and an object of the invention is to provide a method for measuring a liquid immersion lithography soluble fraction in an organic film (hereinafter, may be also referred to as merely "measuring method"), which can improve detection sensitivity of the component exuded from the organic film into the liquid immersion medium used in a liquid immersion lithography method, and which can analyze to evaluate an organic film that can be used in liquid immersion lithography.

In addition, another object of the present invention is to provide: a method for producing a material for forming an organic film, which comprises the above measuring method as a quality control step in its production step: and a material for forming an organic film obtained by this method for production.

Means for Solving the Problems

The present inventors found that by mounting a droplet of a liquid immersion medium on a surface of an organic film formed on a substrate, a component in the organic film can be transferred into the droplet, and that by measuring the soluble fraction in the droplet, quantitative determination of the component in the organic film which was exuded into the liquid immersion medium, and the component which can be exuded is enabled. Thus, the completion of the present invention was achieved.

More specifically, in an aspect of the present invention, a method for measuring a liquid immersion lithography soluble fraction in an organic film including steps of: mounting a droplet of a liquid immersion medium for liquid immersion lithography on a surface of an organic film formed on a substrate; and transferring a component in the organic film into this droplet is provided.

Furthermore, in another aspect of the present invention, a quality control method of a material for forming an organic film for liquid immersion lithography which includes the measuring method described above; and a method for producing a material for forming an organic film for liquid immersion lithography which includes this quality control method are provided. Still further, a material for forming an organic film produced by this method for production is provided.

The term "exudation (elution)" herein refers to a phenomenon of transferring a constituent component in an organic film such as a resist film or a protective film into a liquid immersion medium or a droplet. Moreover, the term "exuded component" refers to a component transferred from the organic film into the liquid immersion medium or the droplet, and captured by the liquid immersion medium or the droplet.

Effects of the Invention

The present invention exhibits beneficial effects as described below by the aforementioned method. In particular, according to the present invention, detection sensitivity of the exuded component from the organic film is significantly improved as compared those of conventional methods. Therefore, determination whether or not the organic film can be used in liquid immersion lithography, i.e., determination of suitability for liquid immersion lithography can be easily and accurately performed.

Furthermore, the measuring method of the present invention can be applied to any liquid immersion media, which may be all types of the liquid immersion medium.

Also, the mass spectrometer is very sensitive and can measure the included component with discrimination, whereby the effects of the present invention can be markedly exhibited.

In addition, liquid chromatography can separate nonionic components in a solution, while a capillary electrophoresis apparatus can separate ionic components in a solution. Therefore, measurement of the exuded components, separately for each component, is enabled, and thus a lot of valid data for determination of suitability for liquid immersion lithography can be obtained.

Moreover, measurement of at least one selected from a solvent, an amine, a photo acid generator cation, a photo acid generator anion, a surfactant, a crosslinking agent and an acid used in forming the organic film included in most of chemically amplified photoresist compositions allows for accurate determination of suitability for liquid immersion lithography of a photoresist composition or a material for forming a protective film.

Additionally, the measuring method described above is applicable to any liquid immersion medium, and particularly, can be incorporated as a quality control step at the end of a production line since any huge equipment is not required. Accordingly, to provide a material for forming the organic film is enabled with a fairly uniform quality.

DETAILED DESCRIPTION OF THE INVENTION

Specific examples of the method for measuring a liquid immersion lithography soluble fraction in an organic film according to the present invention will be described in more detail below by way of Examples and Comparative Examples. The specific examples demonstrated below merely illustrate a method for measuring a liquid immersion lithography soluble fraction in an organic film in attempts to put the technical idea of the present invention into practice, and limitation of the present invention to the specific examples is not intended. Thus, the present invention can be equivalently applied to a variety of modifications and alterations without departing from the technical spirit set forth in the appended claims.

[Method for Measuring Liquid Immersion Lithography Soluble Fraction in Organic Film]

An apparatus for bringing a droplet of a liquid immersion medium for liquid immersion lithography into contact with a surface of a photoresist film, or a protective film provided on the photoresist film (hereinafter, may be merely referred to as "protective film") formed on a substrate used in this embodiment while moving thereon (hereinafter, referred to as "apparatus for sampling exuded component") is first explained. The means for sampling exuded component utilizes "apparatus for testing surface residual metal VRC310S" manufactured by S.E.S. Co., LTD., and the principle of its operation is as described in Patent Document 5.

The method for measuring a liquid immersion lithography soluble fraction in an organic film according to the present invention includes a mounting step, and a transfer step. The "mounting step" refers to a step for mounting a droplet of a liquid immersion medium for liquid immersion lithography on a surface of an organic film formed on a substrate.

Figure 1:
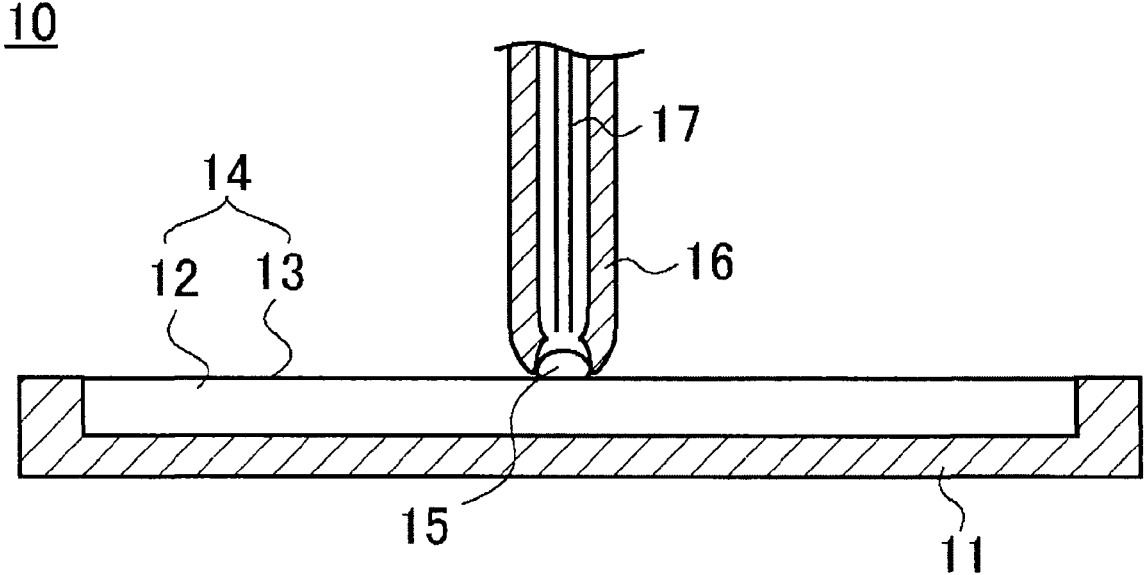
FIG. 1 shows a schematic cross-sectional view illustrating an apparatus for sampling exuded component used in the present invention.

The mounting step is carried out with an apparatus for sampling exuded component 10 as illustrated in a cross-sectional view shown in FIG. 1. First, substrate with organic film 14 obtained by forming an organic film 13 such as a photoresist film and/or a protective film on the surface of substrate 12 (hereinafter, may be merely referred to as "substrate with organic film") is provided on test substrate holder 11 that is fixed on a substrate turntable (not shown in the figure), and droplet 15 of a liquid immersion medium is mounted on the surface of the substrate with organic film 14 while retaining in droplet retainer 16. In this process, the shape of the droplet 15 of the liquid immersion medium becomes spherical on the substrate with organic film 14 as shown in the figure.

The substrate 12 is preferably a silicon semiconductor wafer, and the droplet 15 is preferably of a liquid immersion medium that is at least one selected from water, an alicyclic hydrocarbon-based medium, a fluorine-based medium, and a silicon-based medium. Furthermore, hydrofluoric acid, a mixture of hydrofluoric acid and nitric acid, a mixture of hydrofluoric acid and hydrogen peroxide, a mixture of hydrochloric acid and hydrogen peroxide, or the like may be used as the droplet 15; however, use of such droplets is not preferred in the present invention since they are strong acids, and cannot be used as the liquid immersion medium for liquid immersion lithography.

In addition, the substrate with organic film 14 employed as a test sample may be obtained by forming a photoresist film or a protective film alone on the surface of the substrate 12, or by laminating a photoresist film, and a protective film thereon.

Next, the "transfer step" refers to a step for transferring a component which can be dissolved from the organic film 13 into the liquid immersion medium, or a component which was already exuded, into the droplet 15 mounted in the mounting step. This transfer step may be carried out by mounting the droplet 15 on a predetermined position on the substrate with organic film 14, and leaving to stand for a predetermined time. However, it may be also carried out by moving the droplet 15 on the surface of the organic film 13 at a constant velocity, as explained below.

Figure 2:
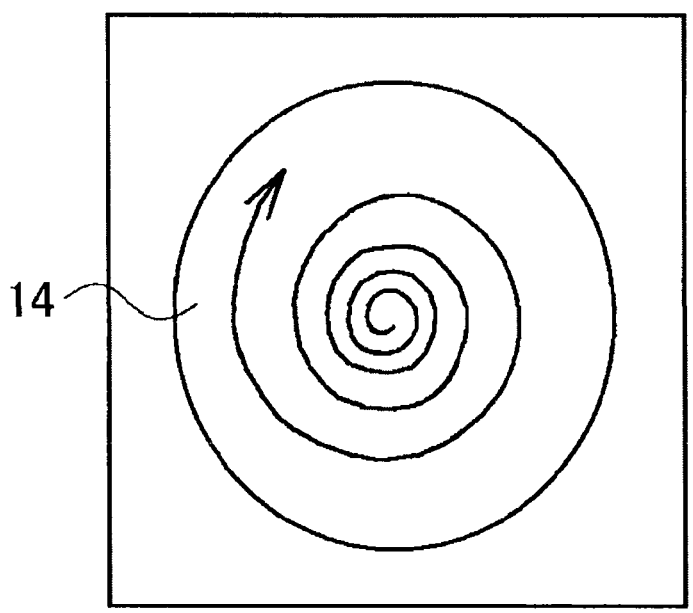
FIG. 2 shows a view illustrating a migration track of a droplet of a liquid immersion medium.

Specifically, as shown in FIG. 2, it is preferred to rotate the substrate with organic film 14 such that the droplet 15 can be scanned and moved at a constant velocity while rotating the substrate with organic film 14. Moreover, it is preferred that the track of the droplet 15 in this step be spiral. Herein, the "constant velocity" may be either an equal linear velocity (tangential velocity) or an equal angular velocity, but an equal linear velocity is preferred. Thus, according as the droplet 15 of the liquid immersion medium mounted on the substrate with organic film 14, the component which can be exuded from the organic film 13 into the liquid immersion medium is absorbed and transferred into the droplet 15 of the liquid immersion medium. An equal linear velocity is employed as the migration velocity of the droplet in order to attain an identical measurement condition for all test samples.

Figure 3:
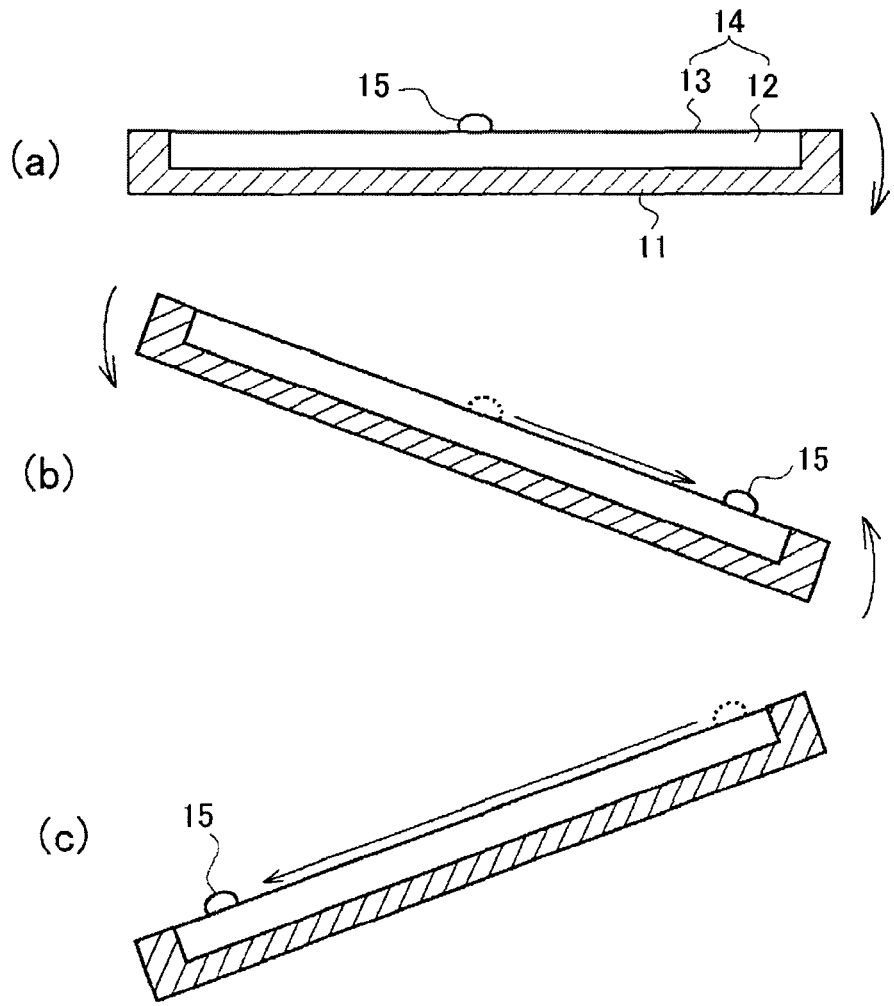
FIGS. 3(a), 3(b) and 3(c) show a cross-sectional view illustrating another process of moving a droplet of the liquid immersion medium.
Figure 4:
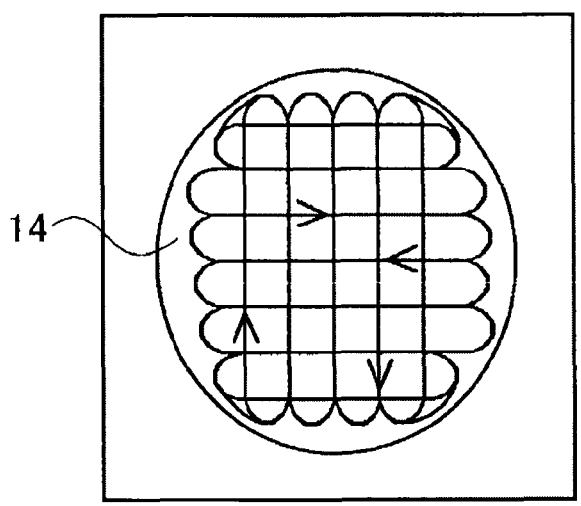
FIG. 4 shows a view illustrating another migration track of the liquid immersion medium.

Also, the droplet 15 of the liquid immersion medium may form a successively repetitive shape as shown in FIG. 4, by moving the substrate with organic film 14 together with the test substrate holder 11 in a variety of directions as illustrated in cross-sectional views shown in FIG. 3(a) to FIG. 3(c).

The "component which can be exuded from the organic film 13 into the liquid immersion medium, or the component which was already exuded" to be transferred into the droplet 15 is preferably at least one selected from a solvent, an amine, a photo acid generator cation, a photo acid generator anion, a surfactant, a crosslinking agent and an acid used in forming the organic film 13.

The measuring method according to the present invention further includes "measurement step" following the "transfer step". The "measurement step" refers to a step for measuring the concentration of the component exuded into the droplet following the transfer step. Specifically, the droplet 15 after the transfer step is collected by declining dropping pipette 17 provided inside the droplet retainer 16 to draw into the droplet retainer 16, and recovering in a certain container not shown in the figure. Thus recovered droplet of the liquid immersion medium is analyzed with a mass spectrometer that is a highly sensitive analysis apparatus to determine the type and amount of the component exuded from the surface of the photoresist film or the protective film. Thus, determination of suitability of the photoresist composition, or the protective film material for liquid immersion lithography is enabled.

The mass spectrometer herein refers to a known analysis apparatus such as a liquid chromatography-mass spectrometer, a capillary electrophoresis-mass spectrometer or the like. Among these, the liquid chromatography-mass spectrometer is preferably used.

[Quality Control Method]

The measuring method according to the present invention can be a quality control method (quality control step) by connecting to a production line of materials for forming an organic film for liquid immersion lithography. Thus, shipping inspection before shipping the product can be conducted.

Figure 5:
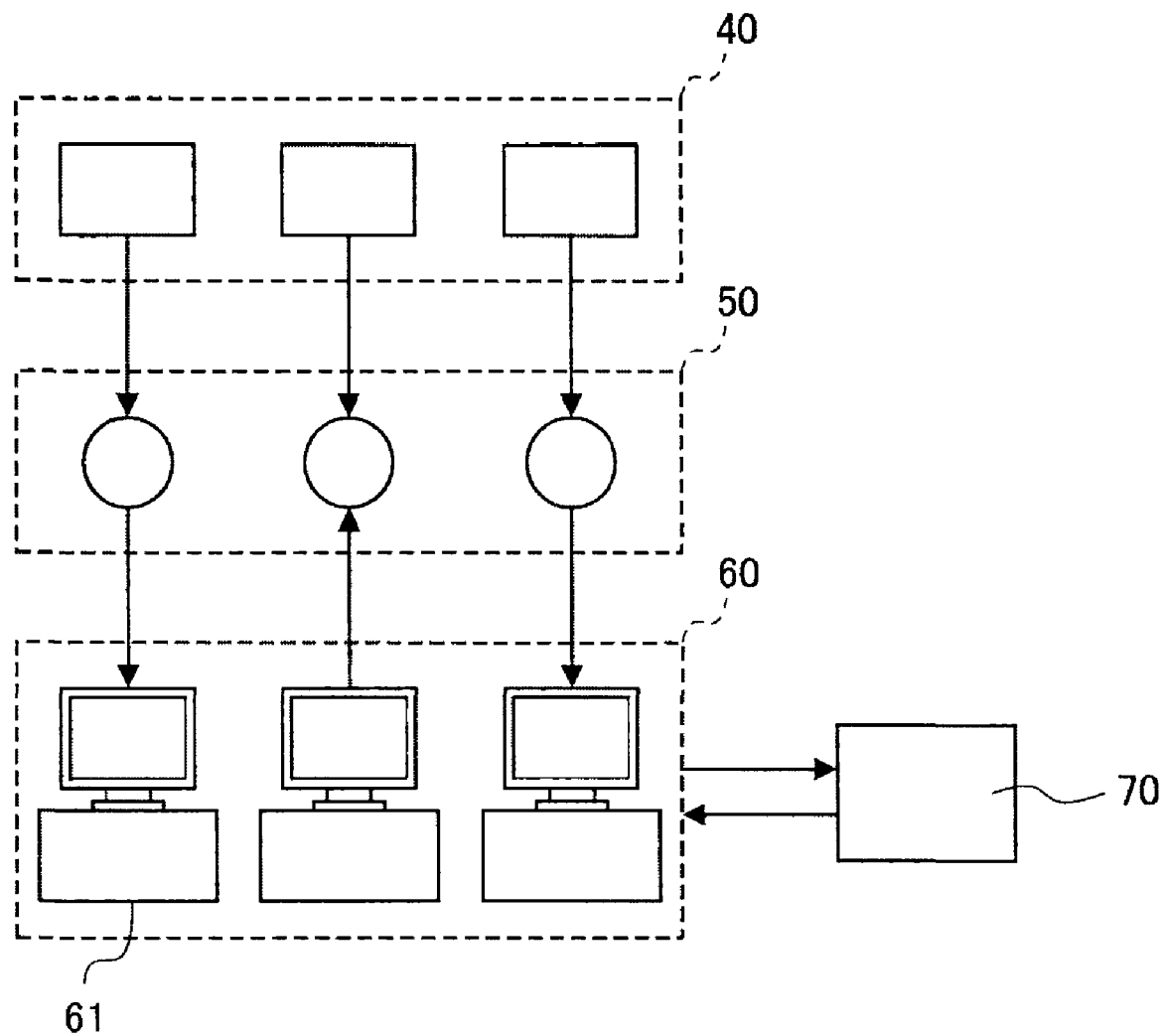
FIG. 5 shows a view illustrating a schematic constitution of the quality control method according to the present invention.
Figure 6:
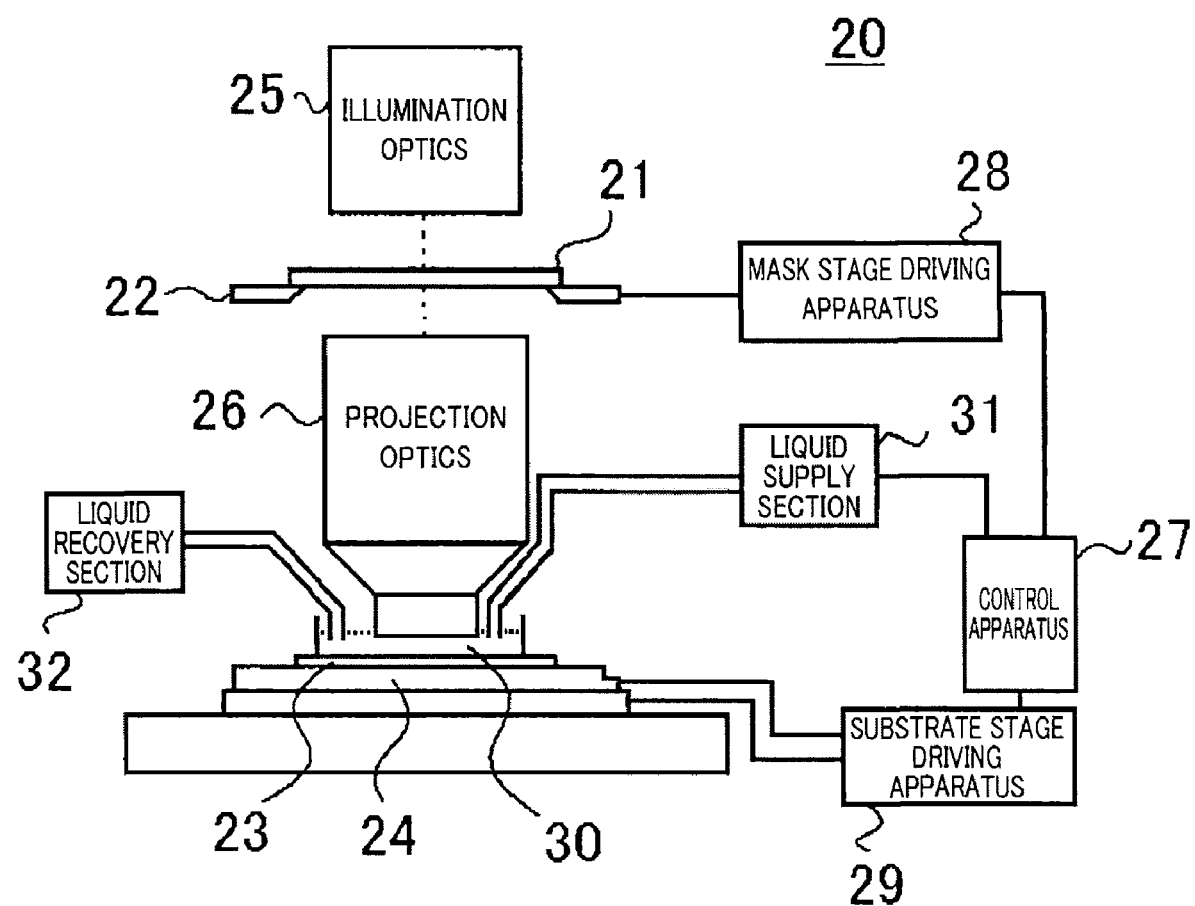
FIG. 6 shows a view illustrating a schematic constitution of an exposure-device for a liquid immersion process.

This quality control method is constituted with product group 40, shipping inspection control group 50, foreign substance inspection device group 60, and database 70, as shown in FIG. 5. The inspection device group 60 herein is constituted with inspection device 61 used in the measuring method according to the present invention. Additionally, inspection results by the inspection device group 60, information in the production process, past case examples of defectives, and the like are stored in the database 70.

Operation of these lines is now explained. First, the product group 40 is produced via each production process along the production line. In final step of the production process, test samples are prepared by applying a predetermined amount of the material for forming the organic film taken from each lot of the product group 40 on a substrate, and these are collected to provide shipping inspection control group 50. This shipping inspection control group 50 is subjected to inspection of foreign substance or fault in the foreign substance inspection device group 60. When the inspection results suggested abnormality, the product is removed. Furthermore, such inspection results are compared with information in the database 70, and coping strategy against the abnormality can be provided as feedback for the production process. The inspection results used in this process may be contents displayed as the inspection results with the inspection device 61 used in the measuring method according to the present invention, and the data obtained by the inspection device 61.

[Method for Producing Material for Forming Organic Film for Liquid Immersion Lithography]

Furthermore, the present invention also relates to a method for producing a material for forming an organic film for liquid immersion lithography (hereinafter, also referred to as material for forming the organic film) which includes the aforementioned quality control method.

The material for forming the organic film refers to a material which can form an organic film such as a photoresist film and a protective film. Specifically, the material involves known materials for forming a resist film, and known compositions for forming a protective film. These are produced via the aforementioned quality control method at a final stage of the production step. Moreover, in this quality control method, the material for forming an organic film determined as negative, i.e., determined as not having suitability for liquid immersion lithography, can be adjusted again for each amount of the component to the extent that the material becomes available as a product. Thus, efficient production of the material for forming the organic film is enabled without need of waste.

The resist composition may be of either positive type or negative type. Any of these contains a photo acid generator (hereinafter, referred to as "PAG"). In the case of the positive type, acid is generated by a reaction upon irradiation with a light having a particular wavelength, and the generated acid allows a dissolution inhibiting group of the resin component having the dissolution inhibiting group to be degraded, thereby turning the exposed part into soluble in an alkali developer. Accordingly, a predetermined positive pattern is formed. To the contrary, in the case of the negative type, an alkali-soluble resin component and a crosslinking agent are included. Acid is generated from the acid generator by a reaction upon irradiation with a light having a particular wavelength, and the generated acid allows the resin component and the crosslinking agent to be crosslinked, thereby turning the exposed part into insoluble in an alkali developer. Accordingly, a negative pattern is formed.

Therefore, these photoresist compositions have been known to result in exudation of PAG cation and PAG anion into the liquid immersion medium, and thus those accompanied by a lower amount of exudation (amount of elution) of at least these compounds can be determined as having suitability for the liquid immersion lithography. In addition, these photoresist compositions usually contain an acid and/or amine quencher, a surfactant, and the like. In particular, these photoresist compositions have been known to result in exudation of amine into the liquid immersion medium, and thus those accompanied by a lower amount of exudation of at least an amine compound can be determined as having suitability for the liquid immersion lithography. Also, those accompanied by a lower amount of exudation of a crosslinking agent, an acid, or a surfactant can be determined similarly as having suitability for the liquid immersion lithography.

Although the resist composition used in the present invention is not particularly limited which may be of either negative type or positive type as described above, to use one of the positive type is more preferred. In particular, a resist composition the base resin of which is a (meth)acrylic ester copolymer having a dissolution inhibiting group on the side chain is preferred.

Furthermore, the protective film material for forming the protective film is not particularly limited, and any known one, for example, those described in Patent Document 6 and Nonpatent Document 1, and the like may be used. Of these, the material preferably includes a polymer containing fluorine as a base resin.

Also in connection with this protective film, the constituent component, or the exuded component similar to that in the photoresist composition may be exuded into the liquid immersion medium via the protective film. Therefore, those accompanied by a lower amount of exudation of such a component can be determined as having suitability for the liquid immersion lithography.

The liquid immersion medium in the present invention is not particularly limited as long as it has a refractive index larger than the refractive index of air. Examples of such a medium include water (pure water), water, alicyclic hydrocarbon-based media, aqueous solutions containing fluorine ion or fluoride ion and having a pH of no greater than 6, aqueous solutions containing ammonium ion and having a pH of no less than 8 (see, Patent Document 3), fluorine-based media (see, Patent Document 4), silicon-based media, and the like. Among these, at least one selected from water (pure water), the fluorine-based media, the silicon-based media is preferably used in light of mass productivity, and the refractive index of the medium.

The fluorine-based medium may be a fluorine-based liquid having a boiling point of 70 to 270° C., and is preferably a perfluoroalkyl ether compound such as perfluoro(2-butyltetrahydrofuran); a perfluoroalkylamine compound such as perfluorotripropylamine, perfluorotributylamine, perfluorotripentylamine or perfluorotrihexylamine, or the like.

Specific examples of the silicon-based medium having such a refractive index include organosiloxanes. The organosiloxanes are represented by the following general formula:

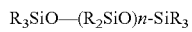

wherein R represents an organic group, and n represents an integer of no less than 0.

In the above general formula, illustrative examples of the organic group R include hydrocarbon groups having 1 to 8 carbon atoms, and halogenated hydrocarbon groups having 1 to 8 carbon atoms. Specific examples of the organic group R include a methyl group, an ethyl group, —$CH_2CH_2CF_3$, and the like. Among them, a methyl group is preferable.

In the above general formula, n is preferably in the range of 0 to 40, more preferably in the range of 0 to 10, further preferably in the range of 0 to 5, particularly preferably in the range of 0 to 2. Most preferably, n is zero (0).

Illustrative commercially available product for use as such a silicon-based liquid may be "SIH6115.0" (refractive index nD25=1.3774, boiling point: 100° C., manufactured by Chisso Corporation), "SIO6703.0" (refractive index nD25=1.3848, boiling point: 153° C., manufactured by Chisso Corporation), "SID2655.0") (refractive index nD25=1.3895, boiling point: 195° C., manufactured by Chisso Corporation), "DMS-T35" (refractive index nD25=1.4035, manufactured by Chisso Corporation), "LS7130" (refractive index nD25=1.3774, boiling point: 100° C., manufactured by Shin-Etsu Silicone Co., Ltd.), "KF-96-5000" (refractive index nD25=1.4035, manufactured by Shin-Etsu Silicone Co., Ltd.), or the like.

EXAMPLES

Production of Sample

Test samples were prepared according to the following procedure. That is, a silicon wafer was used as a substrate, and a chemically amplified photoresist composition having the following composition was used to spin coat as a photoresist composition on the surface thereof. Thereafter, preexposure baking was carried out at 130° C. for 90 sec. Thus resulting photoresist film had a thickness of 200 nm. This photoresist film was employed as substrate sample with photoresist 1.

Next, a protective film material having the following composition was used to spin coat on the surface of the substrate sample with photoresist 1, and then preexposure baking was carried out at 90° C. for 60 sec. Thus obtained protective film had a thickness of 70 nm. This film was employed as substrate sample with protective film 2.

In the chemically amplified photoresist composition, a copolymer (mass average molecular weight: 7000, dispersity index: 2.0) consisting of 30% by mole of a 2-methyl-2-adamantyl methacrylate unit, 50% by mole of an α-(γ-butyrolactonyl) methacrylate unit, and 20% by mole of a 3-hydroxy-(1-adamantyl) acrylate unit was used as a resin component. Each compound is represented by the formula as follows.

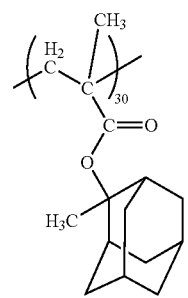

2-methyl-2-adamantyl methacrylate

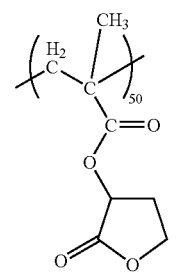

α-(γ-butyrolactonyl) methacrylate

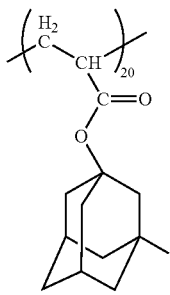

3-hydroxy-(1-adamantyl) acrylate

As the acid generator component, triphenylsulfonium nonafluorobutane sulfonate and 3-methylphenyldiphenylsulfonium trifluoromethane sulfonate were used. These were used in an amount of 3.5 parts by mass and 1.0 part by mass per 100 parts by mass of the above resin, respectively.

In addition, triethanolamine was used as a quencher component, in an amount of 0.3 parts by mass per 100 parts by mass of the resin, and a mixed solvent of propylene glycol monomethyl ether acetate (PGMEA) and ethyl lactate (EL) (mass ratio of 60:40) was used as a solvent in an amount of 1400 parts by mass per 100 parts by mass of the resin.

Mixture of all these components was employed as a chemically amplified photoresist composition.

In addition, a polymer containing fluorine having fluorine and an alicyclic group substituted with a hydroxyl group on the main chain was used as the resin component of a protective film material, and isobutanol was used as a solvent. These were prepared by adding 2200 parts by mass of the solvent to 100 parts by mass of the resin component.

Example 1

In Example, the aforementioned apparatus for sampling exuded component was used, and one drop (200 μL) of pure water was mounted on each surface of the substrate sample with photoresist 1 and the substrate sample with protective film 2 produced as described above. The droplet was moved at an equal linear velocity according to the method shown in FIG. 2 and FIG. 4 at room temperature for 5 min. Thereafter, the droplet was collected with a dropping pipette, and analyzed according to a common procedure with a liquid chromatography-mass spectrometer (LC-MS). The amount of exudation (mol/cm$^2$) of the photoresist film or the protective film per unit area was determined. The results are shown in Table 1 together with detection limit determined by a dilution method.

Comparative Example 1

In Comparative Example, 30 mL of pure water was uniformly spread on each surface of the substrate sample with photoresist 1 and the substrate sample with protective film 2 produced as described above, and stood still at room temperature for 5 min. Thereafter, the entirety of the pure water was recovered, concentrated, and analyzed according to a common procedure with LC-MS and a capillary electrophoresis-mass spectrometer (CE-MS). The amount of exudation of the photoresist film or the protective film per unit area was determined. The results are shown in Table 2 together with detection limit determined by a dilution method.

TABLE 1

| Example | | Sample 1 | Sample 2 | Detection limit (mol/cm$^2$) |
|---|---|---|---|---|
| Detected component | Amine | $8.33 \times 10^{-14}$ | $5.10 \times 10^{-15}$ | $1.70 \times 10^{-15}$ |
| | PAG cation | $2.52 \times 10^{-11}$ | $6.78 \times 10^{-16}$ | $6.78 \times 10^{-15}$ |
| | PAG anion | $1.70 \times 10^{-11}$ | $2.22 \times 10^{-17}$ | $8.50 \times 10^{-16}$ |

PAG: Photo Acid Generator

TABLE 2

| Comparative Example | | Sample 1 | Sample 2 | Detection limit (mol/cm$^2$) |
|---|---|---|---|---|
| Detected component | Amine | $4.00 \times 10^{-13}$ | UDL | $6.00 \times 10^{-14}$ |
| | PAG cation | $5.85 \times 10^{-11}$ | UDL | $3.40 \times 10^{-12}$ |
| | PAG anion | $5.52 \times 10^{-11}$ | UDL | $3.20 \times 10^{-12}$ |

PAG: Photo Acid Generator
UDL: Under Detection Limit

Comparison of the results shown in Table 1 and Table 2 reveals as in the following. With respect to the sample 1, it is proven that detectivity (sensitivity) was improved for all components in Example, and the components could be extracted efficaciously from the photoresist film with high sensitivity. Also with respect to the sample 2, the components which could not be detected in Comparative Example could be measured for all the components in Example due to significantly lowered detection limit.

Therefore, it is revealed that according to the measuring method of Example, detection of a soluble fraction which could not be detected by a conventional measuring method is enabled owing to lowering of the detection limit, i.e., improvement of the detection sensitivity. This suggests that according to the measuring method of Example, in spite of extremely low amount of the droplet of the used liquid immersion medium, an effect could be exhibited which was equivalent to or better than the case in which the exuded component was substantially concentrated in the droplet, since the exuded component was dissolved from a wide area on the surface of the photoresist film or the protective film. Therefore, according to the method of the present invention, suitability of a photoresist composition or a protective film material for liquid immersion lithography can be easily and accurately determined at a low cost, since currently available apparatus can be used without need of separately developing an apparatus for the measurement.

Although examples in which pure water was used as the liquid immersion medium are demonstrated in the present Example and Comparative Example, the present invention is not limited thereto, and can be applied to the cases with known aqueous solutions containing fluorine ion or fluoride ion and having a pH of no greater than 6, aqueous solutions containing ammonium ion and having a pH of no less than 8, fluorine-based media, as well as silicon-based media, and the like. Furthermore, although an amine compound, PAG cation and PAG anion were measured as the component to be detected in the aforementioned examples, the component to be measured may be appropriately selected and measured since the component which will be dissolved from the composition of the used photoresist composition or protective film material can be readily supposed.

The invention claimed is:

1. A method for measuring a liquid immersion lithography soluble fraction in an organic film by measuring the concentration of a component exuded from the organic film formed on a substrate to a liquid immersion medium in a liquid immersion lithography process, the method comprising:
   a mounting step of mounting a droplet of a liquid immersion medium for liquid immersion lithography on a surface of the organic film formed on a substrate;
   a transfer step of transferring the component in the organic film into the droplet; and
   after the transfer step, a measuring step of measuring the concentration of the component exuded into the droplet.

2. The method for measuring a liquid immersion lithography soluble fraction in an organic film according to claim 1 wherein the transfer step is a step of transferring the component in the organic film into the droplet while moving the droplet on the surface of the organic film at a constant velocity.

3. The method for measuring a liquid immersion lithography soluble fraction in an organic film according to claim 1 further comprising a measuring step of measuring the concentration of the component exuded into the droplet following the transfer step.

4. The method for measuring a liquid immersion lithography soluble fraction in an organic film according to claim 1 wherein the liquid immersion medium for liquid immersion lithography is a medium having a refractive index larger than the refractive index of air.

5. The method for measuring a liquid immersion lithography soluble fraction in an organic film according to claim 1 wherein the liquid immersion medium for liquid immersion lithography is at least one selected from water, an alicyclic hydrocarbon-based medium, a fluorine-based medium, and a silicon-based medium.

6. The method for measuring a liquid immersion lithography soluble fraction in an organic film according to claim 1 wherein the organic film is at least one of a photoresist film and a protective film provided on the photoresist film.

7. The method for measuring a liquid immersion lithography soluble fraction in an organic film according to claim 1 wherein the concentration of the component exuded into the droplet is measured using a mass spectrometer.

8. The method for measuring a liquid immersion lithography soluble fraction in an organic film according to claim 7 wherein the concentration of the component exuded into the droplet is measured using at least one of a liquid chromatography-mass spectrometer and a capillary electrophoresis-mass spectrometer.

9. The method for measuring a liquid immersion lithography soluble fraction in an organic film according to claim 1 wherein the component exuded into the droplet to be measured is at least one selected from a solvent, an amine, a photo acid generator cation, a photo acid generator anion, a surfactant, a crosslinking agent and an acid used in forming the organic film.

10. A quality control method of a material for forming an organic film for liquid immersion lithography, which comprises:
   a step of collecting a predetermined amount of the material for forming the organic film for liquid immersion lithography taken from each lot of a product group in a final step of a production process, a product group produced via each production process along a production line;
   a step of measuring a liquid immersion lithography soluble fraction according to the method of claim 1 on a shipping inspection control group provided by collecting test samples prepared by applying on the substrate the material for forming the organic film collected in the collecting step, and
   a step of removing an abnormal product based on the above measurement results.

* * * * *